(12) United States Patent
Eckhouse et al.

(10) Patent No.: US 8,702,769 B2
(45) Date of Patent: Apr. 22, 2014

(54) SAFE SKIN TREATMENT APPARATUS FOR PERSONAL USE AND METHOD FOR ITS USE

(75) Inventors: Shimon Eckhouse, Haifa (IL); Lion Flyash, Nazareth Illit (IL); Boris Vaynberg, Zichron Yaakov (IL)

(73) Assignee: Syneron Medical Ltd, Yokneam (IL)

( * ) Notice: Subject to any disclaimer, the term of this patent is extended or adjusted under 35 U.S.C. 154(b) by 16 days.

(21) Appl. No.: 12/663,575

(22) PCT Filed: Sep. 3, 2009

(86) PCT No.: PCT/IL2009/000856
§ 371 (c)(1),
(2), (4) Date: Dec. 8, 2009

(87) PCT Pub. No.: WO2010/029536
PCT Pub. Date: Mar. 18, 2010

(65) Prior Publication Data
US 2011/0245735 A1 Oct. 6, 2011

Related U.S. Application Data

(60) Provisional application No. 61/095,973, filed on Sep. 11, 2008, provisional application No. 61/107,744, filed on Oct. 23, 2008.

(51) Int. Cl.
*A61N 5/06* (2006.01)

(52) U.S. Cl.
USPC ......... 607/88; 607/89; 607/90; 607/91; 607/92; 607/93; 607/94; 607/95; 607/96; 607/98; 607/99; 607/100; 607/101; 607/102; 607/112; 606/2; 606/3; 606/4; 606/5; 606/6; 606/7; 606/8; 606/9; 606/10; 606/11; 606/12; 606/13; 606/14; 606/15; 606/16; 606/17; 606/18; 606/19; 606/27; 606/28

(58) Field of Classification Search
USPC ............ 607/88–102, 112; 606/2–19, 27–52
See application file for complete search history.

(56) References Cited

U.S. PATENT DOCUMENTS

| | | | |
|---|---|---|---|
| 7,141,049 B2 * | 11/2006 | Stern et al. ............... | 606/41 |
| 7,251,531 B2 | 7/2007 | Mosher et al. | |
| 8,133,191 B2 * | 3/2012 | Rosenberg et al. ........ | 601/2 |
| 8,273,037 B2 * | 9/2012 | Kreindel et al. ........... | 601/6 |
| 8,292,882 B2 * | 10/2012 | Danek et al. .............. | 606/34 |
| 2001/0014819 A1 | 8/2001 | Ingle et al. | |
| 2003/0199863 A1 * | 10/2003 | Swanson et al. .......... | 606/40 |
| 2006/0173518 A1 | 8/2006 | Kreindel | |
| 2008/0004678 A1 | 1/2008 | Kreindel | |

(Continued)

OTHER PUBLICATIONS

Written opinion of the international searching authority mailed on Mar. 3, 2010.

*Primary Examiner* — Tod T Van Roy
*Assistant Examiner* — Delma R Forde
(74) *Attorney, Agent, or Firm* — Smith Risley Tempel Santos LLC; Gregory Scott Smith

(57) ABSTRACT

A technique for detecting and providing alerts or indications that can be used for controlling or altering the displacement speed of an applicator coupling skin heating energy across a treated skin. A temperature sensor monitors the rate of skin temperature change and provides feedback related to altering the applicator displacement speed according to the rate of skin temperature change. Disclosed is also an applicator for implementing this method.

16 Claims, 11 Drawing Sheets

(56) References Cited

U.S. PATENT DOCUMENTS

| | | | |
|---|---|---|---|
| 2008/0139974 A1* | 6/2008 | Da Silva | 601/3 |
| 2009/0192503 A1* | 7/2009 | Epshtein et al. | 606/15 |
| 2010/0211055 A1* | 8/2010 | Eckhouse et al. | 606/9 |
| 2010/0249772 A1* | 9/2010 | Mehta et al. | 606/41 |
| 2011/0015549 A1* | 1/2011 | Eckhouse et al. | 601/3 |
| 2012/0022518 A1* | 1/2012 | Levinson | 606/33 |
| 2012/0197242 A1* | 8/2012 | Rosenberg | 606/2 |
| 2012/0290023 A1* | 11/2012 | Boyden et al. | 607/3 |
| 2013/0144280 A1* | 6/2013 | Eckhouse et al. | 606/9 |
| 2013/0289679 A1* | 10/2013 | Eckhouse et al. | 607/102 |

* cited by examiner

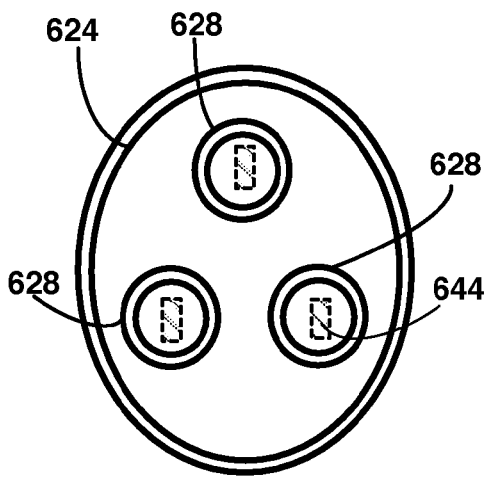
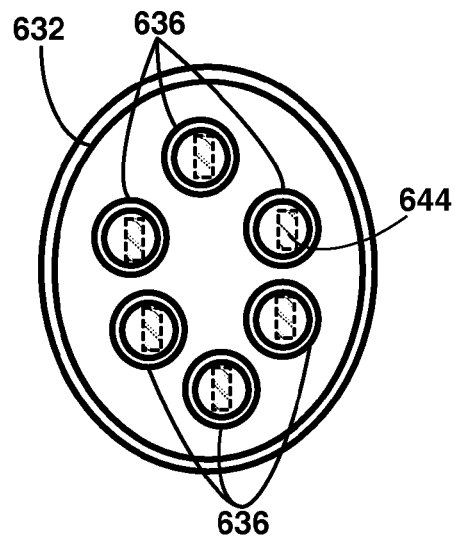
FIG. 6C    FIG. 6D
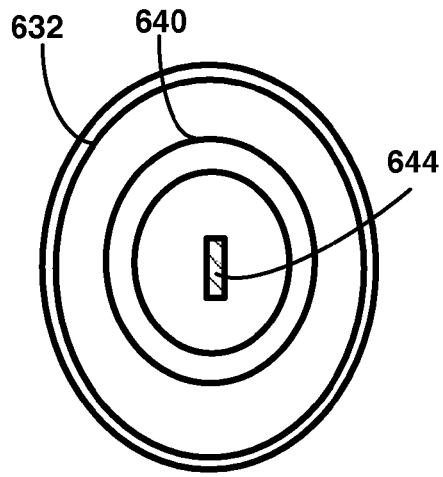
FIG. 6E

SAFE SKIN TREATMENT APPARATUS FOR PERSONAL USE AND METHOD FOR ITS USE

CROSS-REFERENCE TO RELATED APPLICATIONS

This application is being filed under 35 U.S.C 371 as a national patent application based on International Application Number PCT/IL2009/000856 filed on Sep. 3, 2009 which application claims priority to U.S. Provisional Application 61/095,973 filed on Sep. 11, 2008 and 61/107,744 filed on Oct. 23, 2008, all of which are hereby incorporated by reference.

TECHNOLOGY FIELD

The method and apparatus relate to the field of skin treatment and personal cosmetic procedures and, in particular, to safe skin treatment procedures.

BACKGROUND

External appearance is important to practically everybody. In recent years, methods and apparatuses have been developed for different cosmetic treatments to improve external appearance. Among these are: hair removal, treatment of vascular lesions, wrinkle reduction, collagen destruction, circumference reduction, skin rejuvenation, and others. In these treatments, a volume of skin to be treated is heated to a temperature that is sufficiently high as to perform the treatment and produce one of the desired treatment effects. The treatment temperature is typically in the range of 38-60 degrees Celsius.

One method used for heating the epidermal and dermal layers of the skin is pulsed or continuous radio frequency (RF) energy. In this method, electrodes are applied to the skin and an RF voltage, in a continuous or pulse mode, is applied across the electrodes. The properties of the voltage are selected to generate an RF induced current in the skin to be treated. The current heats the skin to the required temperature and causes a desired effect, performing one or more of the listed above treatments.

Another method used for heating the epidermal and dermal layers of the skin is illuminating the skin segment to be treated by optical, typically infrared (IR) radiation. In this method, a segment of skin is illuminated by optical radiation in a continuous or pulse mode. The power of the radiation is set to produce a desired skin effect. The IR radiation heats the skin to the required temperature and causes one or more of the desired effects.

An additional method used for heating the epidermal and dermal layers of the skin is application of ultrasound energy to the skin. In this method, ultrasound transducers are coupled to the skin and ultrasound energy is applied to the skin between the transducers. The properties of the ultrasound energy are selected to heat a target volume of the skin (usually the volume between the electrodes) to a desired temperature, causing one or more of the desired treatment effects, which may be hair removal, collagen destruction, circumference reduction, skin rejuvenation, and others.

Methods exist which simultaneously apply a combination of one or more skin heating techniques to the skin. Because all of the methods alter the skin temperature, monitoring of the temperature is frequently used to control the treatment. In order to continuously monitor skin temperature, suitable sensors such as a thermocouple or a thermistor could be built into the electrodes or transducers through which the energy is applied to the skin. Despite the temperature monitoring, certain potential skin damage risks still exist, since the sensor response time depends on heat conductivity from the skin to the sensor and inside the sensor, and may be too long and even damaging to the skin before the sensor reduces or cuts off the skin heating power. To some extent, this risk can be avoided by reducing the cut-off temperature limit operating the sources of optical radiation, RF energy, and ultrasound energy. However, this would limit the RF energy transmitted to the skin and the treatment efficacy. In some instances, for example, when the applicator is static, the temperature of the skin (and of the electrodes) may increase fast enough to cause skin damage.

The devices delivering energy to the skin, such as electrodes, transducers and similar are usually packed in a convenient casing, an applicator, operative to be held and moved across the skin. The user has to adjust applicator movement speed to a given constant skin heating energy supply, such as to enable optimal or proper skin treatment. However, at present the user has no indication if the selected applicator speed is proper or not.

There is a need to provide a method to alert or signify the user as early as possible of the undesired skin or electrode temperature changes. There is also a need to allow the user to adapt applicator movement speed at constant skin heating energy supply, enabling optimal or proper skin treatment. This is especially important for the fast developing field of personal skin treatment apparatuses enabling their safe use, as the typical user of such apparatus may be inexperienced.

BRIEF SUMMARY

When heating energy is applied to a segment of skin to be treated and the applicator is displaced from one segment of skin to another, there is a difference in the rate of the skin temperature increase or change, which depends on the speed of displacement of the applicator. When the applicator is moved too quickly, the rate at which the temperature of the skin increases is significantly lower than the rate of temperature increase in the course of "proper" applicator movement speed. A high rate of temperature change is indicative of a static applicator, a condition that may cause burns, blisters and other skin damage. Proper speed of displacement of the applicator may therefore be achieved by controlling the rate of the skin temperature change.

BRIEF LIST OF DRAWINGS

The apparatus and the method are particularly pointed out and distinctly claimed in the concluding portion of the specification. The apparatus and the method, however, both as to organization and method of operation, may best be understood by reference to the following detailed description when read with the accompanying drawings, in which like reference characters refer to the same parts throughout the different views. The drawings are not necessarily to scale, emphasis instead being placed upon illustrating the principles of the method.

FIG. 1 is a schematic illustration of an exemplary embodiment of the apparatus for personal skin treatment.

FIGS. 2A and 2B, collectively referred to as FIG. 2, are schematic illustrations of front and side views of the first exemplary embodiment of the present applicator configured to apply RF energy to a segment of skin.

FIG. 3 is a graphic illustration or plot of the skin (and RF electrodes) temperature dependence on the speed of applicator displacement.

FIGS. 4A and 4B, collectively referred to as FIG. 4, are schematic illustrations of full and insufficient contact of the electrode with a segment of skin.

FIG. 5 is an exemplary schematic illustration of the dependence of skin impedance on the quality of electrode-skin contact.

FIGS. 6A-6E-are schematic illustrations of some exemplary configurations of the electrodes of the present applicator.

FIGS. 7A and 7B are schematic illustrations of a second exemplary embodiment of the present applicator including a skin temperature probe configured to measure the level of RF energy applied to a segment of skin.

FIGS. 8A and 8B, collectively referred to as FIG. 8, are schematic illustrations of a third exemplary embodiment of the present applicator configured to apply RF energy and optical radiation to a segment of skin.

DETAILED DESCRIPTION OF EXEMPLARY EMBODIMENTS

In the following detailed description, reference is made to the accompanying drawings that form a part hereof. This is shown by way of illustration of different embodiments in which the apparatus and method may be practiced. Because components of embodiments of the present apparatus can be in several different orientations, the directional terminology is used for purposes of illustration and is in no way limiting. It is to be understood that other embodiments may be utilized, and structural or logical changes may be made without departing from the scope of the present method and apparatus. The following detailed description, therefore, is not to be taken in a limiting sense, and the scope of the present apparatus and method is defined by the appended claims.

As used herein, the term "skin treatment" includes treatment of various skin layers such as stratum corneum, dermis, epidermis, skin rejuvenation procedures, wrinkle removal, and such procedures as hair removal and collagen shrinking or destruction.

The term "skin surface" relates to the most external skin layer, which may be stratum corneum, epidermis, or dermis.

As used herein, the term "rate of temperature change" means a change of the skin or electrode temperature measured in temperature units per time unit.

The term "skin heating energy" incorporates RF energy, ultrasound energy, optical radiation, and any other form of energy capable of heating the skin.

Figure 1:
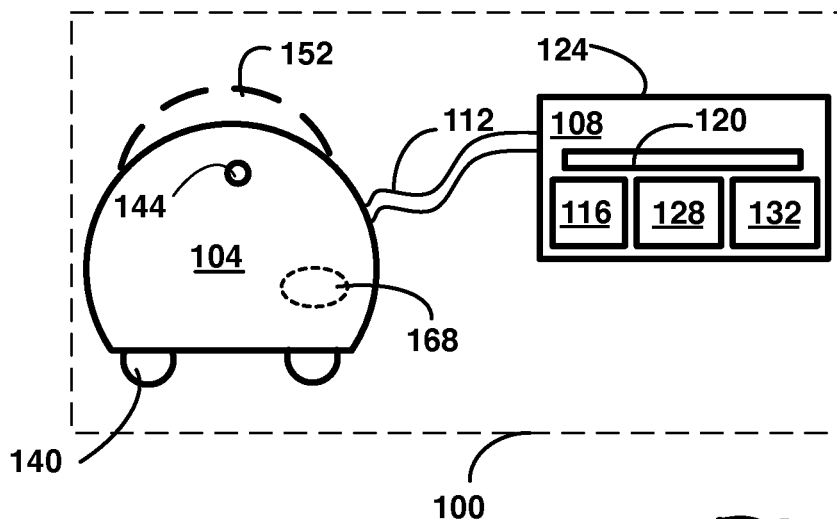

Reference is made to FIG. 1, which is a schematic illustration of a first exemplary embodiment of the apparatus for safe skin treatment. Apparatus 100 comprises an applicator 104 operative to slide along a subject skin (not shown), a control unit 108 controlling the operation of apparatus 100, and a harness 112 connecting between applicator 104 and control unit 108. Harness 112 enables electric, fluid, and other type of communication between applicator 104 and control unit 108.

Control unit 108 may include a source of skin heating energy 116. A few non-limiting examples of a source of skin heating energy include an RF energy generator, a source of optical radiation, or a source of ultrasound energy. Control unit 108 may include control electronics that may be implemented as a printed circuit board 120 populated by proper components. Board 120 may be located, together with control unit 108, in a common packaging 124. Board 120 may include a feedback loop 128 configured to monitor, during the course of operation, the quality of the skin heating energy applied by the skin coupling, and a feedback loop 132 for monitoring the temperature of a segment of treated skin and deriving there from the rate of temperature change. The term coupling as applied to various probes and devices with skin within this description refers to creating contact with the skin in such a way that energy can be transferred to the skin or measurements can be taken. Apparatus 100 may receive power supply from a regular electric supply network receptacle, or from a rechargeable or conventional battery based supply.

Applicator 104 may include one or more RF energy supplying electrodes 140, visual skin treatment progress indicator 144, and an audio skin treatment progress indicator 168. The indicators may be configured to inform or signify to the user the status of interaction of the RF energy with the skin, and alert the user with regards to undesirable applicator displacement speed or RF energy variations. For example, if the applicator displacement speed is slower than the desired or proper displacement speed, an audio process progress indicator will alert or signify the user by way of audio signal. The visual status indicator may be operative to indicate to or alert the user with a signal that the applicator displacement speed is higher than the desired displacement speed. Any other combination of audio and visual process progress indicator operation is possible.

Figure 2A:
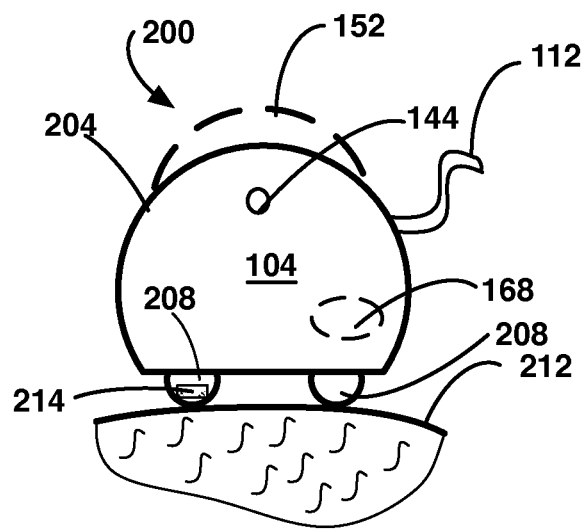
Figure 2B:
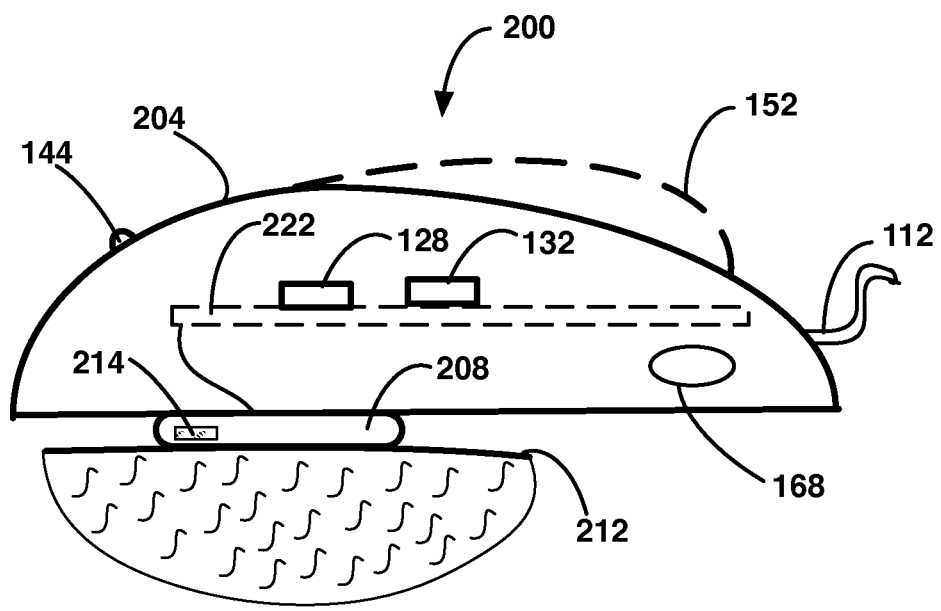

FIGS. 2A and 2B are schematic illustrations of a front view (FIG. 2A) and a side view (FIG. 2B) of a second exemplary embodiment of the present applicator. Applicator 200 includes a convenient to hold case 204 incorporating one or more electrodes 208 operative to apply safe levels of skin heating energy to a subject skin 212. The skin heating energy in this particular case is RF energy. A temperature sensor such as, for example, a thermistor or a thermocouple 214 is built into one or more electrodes 208 and is operative to provide the electrode temperature reading to a feedback loop 132 operating an RF energy-setting control circuit, which may be implemented as a printed circuit board 222.

Figure 3:
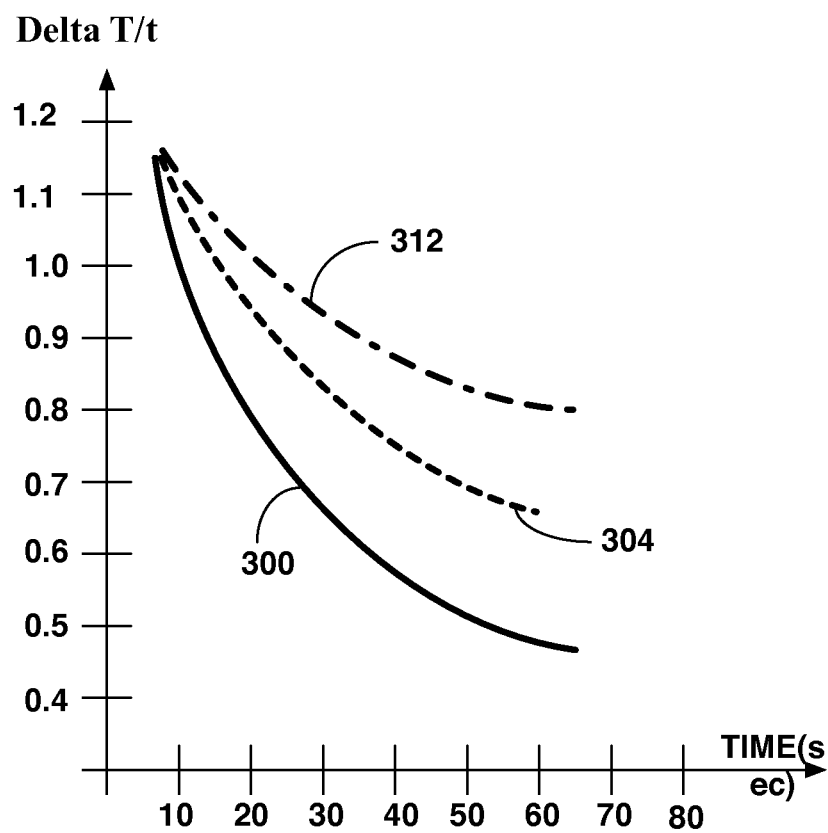

It has been experimentally discovered that the temperature change of (a) the skin segment located between the RF electrodes and (b) the electrodes in contact with the skin at a constant skin heating energy level, depends on the applicator displacement speed. FIG. 3 graphically illustrates the skin and RF electrodes temperature dependence on the applicator displacement speed. Curve 300 illustrates the rate of temperature change for a static applicator. Curves 304 and 312 illustrate the rate of temperature change as a function of the applicator displacement speed. The applicator displacement speed was respectively 5 cm/sec and 10 cm/sec for curves 304 and 323. (The graphs are given for a thermistor with a negative temperature coefficient.) Although the present graphs are based on the use of a thermistor, non-limiting examples of other temperature detectors include termocouples, resistance temperature detectors (RTD), and non-contact optical detectors such as a pyrometer and similar devices. The thermistor was selected because it possesses higher precision within a limited temperature range and a faster response time.

Referring once again to FIG. 1 (circuit board 120), and FIGS. 2A and 2B (control circuit 222) include a feedback loop mechanism 132 configured to generate a rate of temperature change based on temperature sensor 214 readings. The rate of temperature change may be measured in degrees (Celsius or any other temperature unit) per time unit. Alternatively, there may be a customized integrated circuit including thermistor 214 and a mechanism of converting temperature into the rate of temperature change. Temperature measurements may be converted into a rate of temperature change using either digital or analog conversion circuits.

Figure 4A:
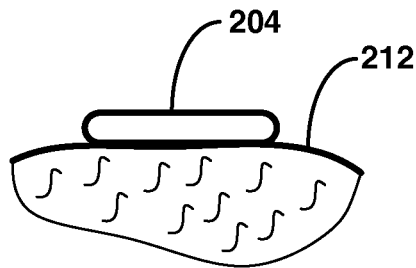
Figure 4B:
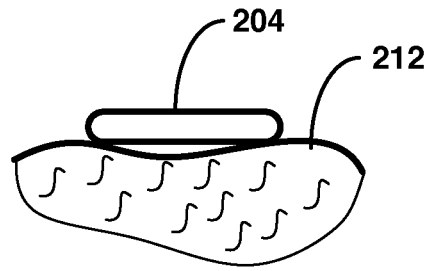

Heat transfer from the skin to the electrode, and accordingly the temperature measured by the temperature sensor, is largely dependent on the quality of the contact between the electrode and the skin. Differences in the quality of the contact can cause a large variability in the temperature measurement. Firm contact between electrodes 208 and subject skin 212, as illustrated in FIG. 4A, supports a short response time of the temperature sensor to the variations in the skin temperature, whereas with poor contact, as illustrated in FIG. 4B, the response time of the temperature sensor may be much longer. In order to improve the RF electrode contact with the skin, a coupling gel can be applied to skin 212 improving, to some extent, heat transfer and RF energy coupling. The gel, however does not completely resolve the problem or compensate for poor or improper electrode-skin contact.

Figure 5:
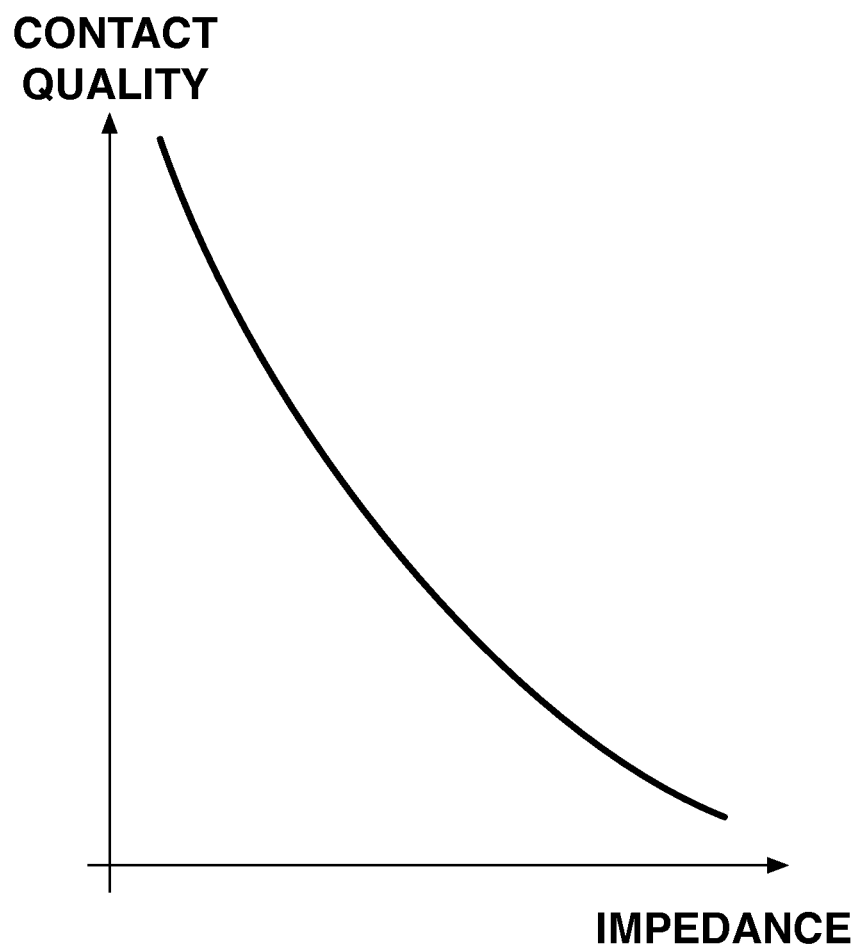

RF energy coupled to the skin induces an electric current that heats the skin. The current is dependent on the skin impedance, which is a function of the quality of the RF electrode contact with the skin. FIG. 5 is an exemplary graphical illustration of the skin impedance dependency on quality of the electrodes with the skin contact. The temperature measured by the sensor is dependent on the actual rate of heat exchange between the electrode and the skin and on the quality of the electrode with the skin contact. Proper contact between electrodes 208 and skin 212 (FIGS. 2A and 2B) may be detected during the treatment by monitoring skin impedance between electrodes 208 as disclosed in the U.S. Pat. No. 6,889,090 awarded to the same assignee as the present disclosure. The impedance measurement is an excellent indicator of the contact quality. Low impedance between electrodes 208 and skin 212 (FIGS. 2A and 2B) means that a firm contact between the electrode and the skin exists and accordingly the temperature sensor can follow the changes in the skin temperature sufficiently quick. Other known impedance monitoring methods may also be applied.

Generally, it is possible to measure the quality of the thermal contact through monitoring the rate of heating (or temperature change) of the temperature sensor (i.e., good contact results in a higher rate of heating). However, the measurements taken would not provide an actual indication as to whether the rate of heating is indeed rapid or slow, because it may be affected by firm or poor electrode-skin contact. The impedance measurement is independent of the temperature sensor measurements. Thus, continuous impedance monitoring provides electrode-skin contact quality and allows the electrode skin thermal contact influence on the rate of temperature change measurement to be eliminated or normalized.

In addressing this issue, control circuit 222 includes a mechanism 128 (FIG. 2B) configured to continuously monitor the skin impedance by measuring the electric current between electrodes 140 (FIG. 1) or 208 (FIGS. 2A and 2B). Continuous monitoring of the quality of contact of the electrodes with the skin eliminates the influence of the electrode-skin contact on the measurements of the rate of temperature variations making the rate of temperature variations an objective indicator of the skin RF energy interaction and treatment status. Thus, regardless of the quality of the contact between the electrodes and the skin, an indication of the rate of temperature variations normalized in this manner provides quality feedback to the user regarding the operation of the apparatus.

Figure 6A:
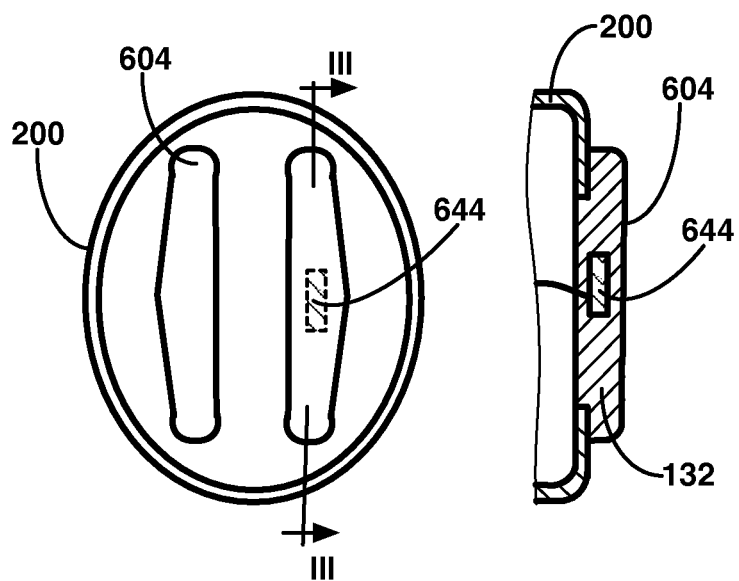
Figure 6B:
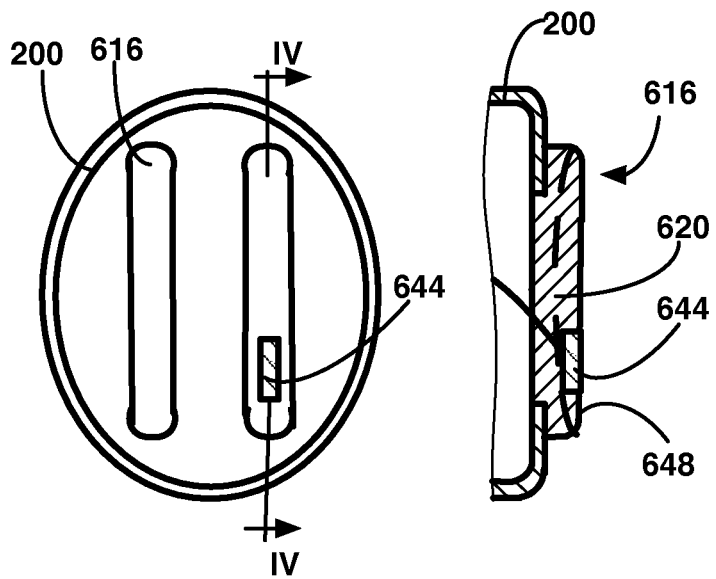

FIGS. 6A, 6B, 6C, 6D and 6E are schematic illustrations of exemplary configurations of the RF electrodes of the present applicator. Electrodes 604 may be elongated bodies of oval, rectangular or other shapes. In one embodiment (FIG. 6A), electrode 604 is a solid electric current conducting body. In another embodiment (FIG. 6B), electrode 616 may be a flexible electric current conducting body. A flexible electrode is capable of adapting its shape, shown by phantom line 620, to the topography of the treated subject skin enabling better contact with the skin. In still a further embodiment, electrode 604 may be a hollow electrode (A hollow electrode generally has a thermal mass smaller than a comparable sized solid electrodes). FIG. 6C shows an applicator 624 containing three equi-shaped electrodes 628. FIG. 6D shows an applicator 632 containing a plurality of equi-shaped electrodes 636. The electrodes may be of round, elliptical, oval, rectangular or other curved shapes, as appropriate for a particular application. The geometry of the electrodes is optimized to heat the skin in the area between the electrodes.

The RF electrodes are typically made of copper or nickel coated aluminum or other metals characterized by good heat conductivity. The electrodes have rounded edges in order to avoid hot spots on the skin surface near the edges of the electrodes. Rounded electrode edges also enable smooth displacement of applicator 104 (FIG. 1) or 204 (FIG. 2) across the skin surface. FIGS. 6A through 6D illustrate bi-polar electrode systems. FIG. 6E illustrates a uni-polar electrode system 640. Each of the electrodes may contain a temperature sensor 644 configured to measure the electrode temperature in course of operation. Temperature sensor 644 may reside inside the electrode or form a continuous plane with one of it surfaces. For example, in FIG. 6B, surface 648 forms direct contact with the skin enabling direct skin temperature measurement.

Figure 7A:
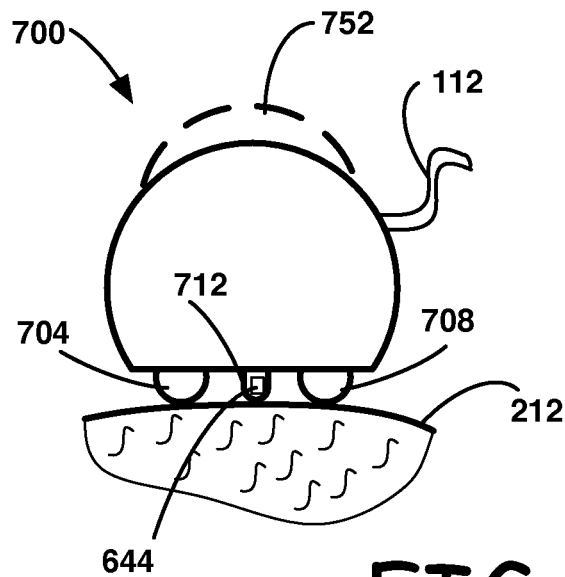
Figure 7B:
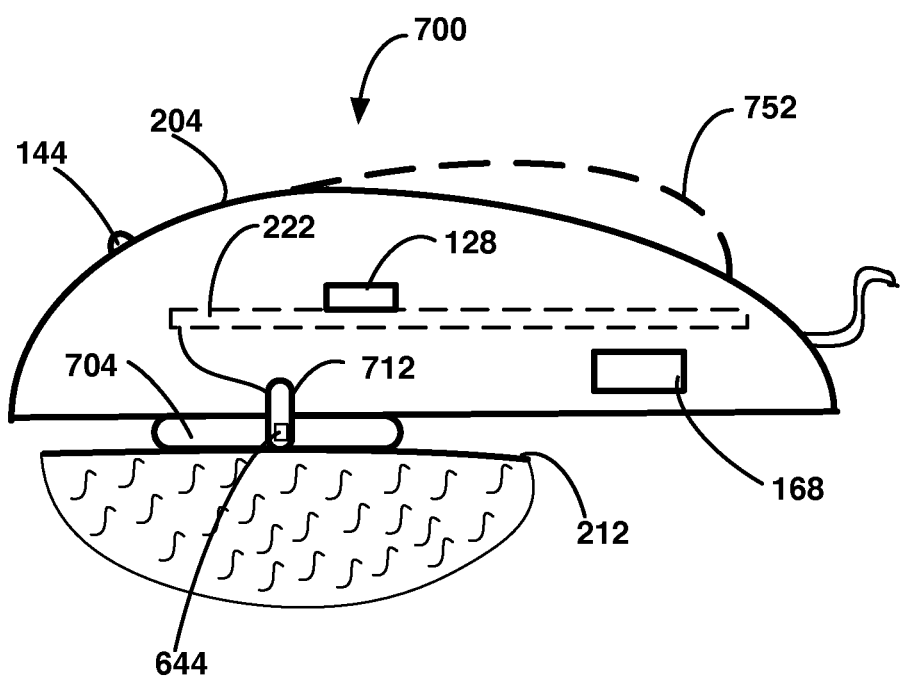

Solid metal electrodes 604 may have a relatively large thermal mass and require time until the correct reading of the temperature sensor 644 is established. FIGS. 7A and 7B are schematic illustrations of another exemplary embodiment of the present applicator. The temperature sensor 644 may be located in a spring-loaded probe 704 having a small thermal mass, compared to the electrodes, and adapted for sliding movement across the subject skin 212. Depending on the size of the skin segment treated, there may be one or more probes 704 with each probe 704 incorporating a temperature sensor 644. Processing of the temperature sensor readings is similar to the processing manner described above and is directed to defining the rate of skin temperature change, or signifying and informing the user of extreme temperature values. Use of a number of probes 704 with each probe 704 incorporating a temperature sensor 644 enables a more accurate temperature measurement and rate of temperature change assessment and a uniform treated skin segment thermal profile mapping.

Electrodes 704, of applicator 700 may be coated with a thin metal layer sufficient for RF energy application, wherein the electrodes themselves may be made of plastic or composite material. Both plastic and composite materials are poor heat conductors and a temperature sensor located in such electrodes would not enable rapid enough temperature reading required for RF energy correction and may not provide a correct reading. The addition of a temperature sensor located in a spring-loaded probe 712 allows rapid temperature monitoring even with plastic electrodes. This simplifies the electrode construction and enables disposal where needed of electrodes 704 for treatment of the next subject, and variation of the shape of the electrodes as appropriate for different skin treatments. In an alternative embodiment, the temperature sensor may be an optical non-contact sensor such as a pyrometer.

A coupling gel can be applied to the skin before applying the RF energy, which to some extent, improves heat transfer and RF energy coupling. Accordingly, applicator 700 may include an optional gel dispenser 752 similar or different from gel dispenser 152 (FIGS. 1 and 2). Gel dispenser 752 may be operated manually or automatically. The gel would typically be selected to have an electrical resistance higher than that of the resistance of the skin. In some embodiments a gel reservoir may reside inside control unit 108 (FIG. 1) and be supplied to the skin to be treated with the help of a pump (not shown).

Figure 8A:
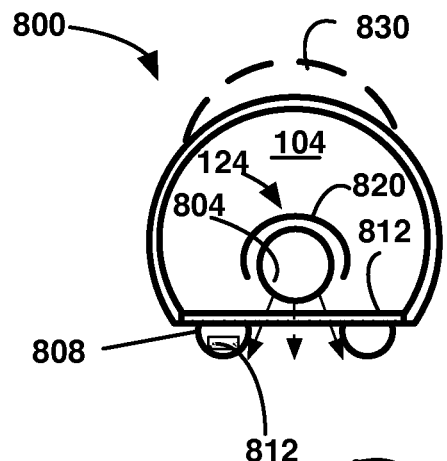
Figure 8B:
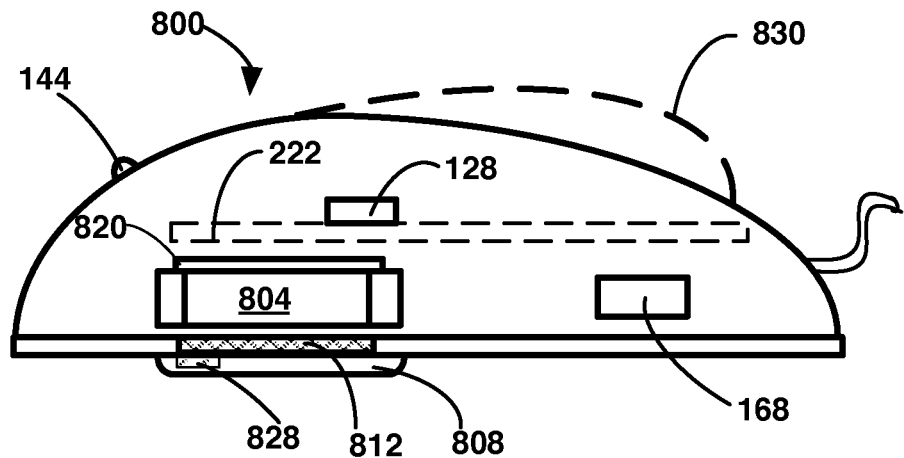

FIG. 8 is a schematic illustration of an additional exemplary embodiment of the present applicator. Applicator 800 includes a source of optical radiation 804 located between electrodes 808 and configured to illuminate at least the segment of the skin located between electrodes 808. The source of optical radiation may be one of a group consisting of incandescent lamps and lamps optimized or doped for emission of red and infrared radiation, and a reflector 820 directing the radiation to the skin, an LED, and a laser diode. The spectrum of optical radiation emitted by the lamps may be in the range of 400 to 2400 nm and the emitted optical energy may be in the range of 100 mW to 20 W. An optical filter 812 may be selected to transmit red and infrared optical radiation in order to transmit a desired radiation wavelength to the skin. Filter 812 may be placed between the skin and the lamp and may serve as a mounting basis for one or more electrodes 808. Reflector 820 collects and directs radiation emitted by lamp 804 towards a segment of skin to be treated. When LEDs are used as radiation emitting sources, their wavelengths may be selected such as to provide the desired treatment, eliminating the need for a special filter. A single LED with multiple wavelength emitters may also be used.

Operation of the source of optical radiation 804 enhances the desired skin effect caused by the RF energy induced current. All electrode structures described above, visual and audio signal indicators are mutatis mutandis applicable to respective elements of applicator 800. A temperature sensor 828 may be located in one or more electrodes 808 or probes similar to probe 712 (FIG. 7A) may be added (not shown) and located so as not to mask optical radiation. A manually or automatically operated gel dispenser 830 similar to gel dispenser 152 (FIGS. 1 and 2) may be part of the applicator 800.

Figure 9:
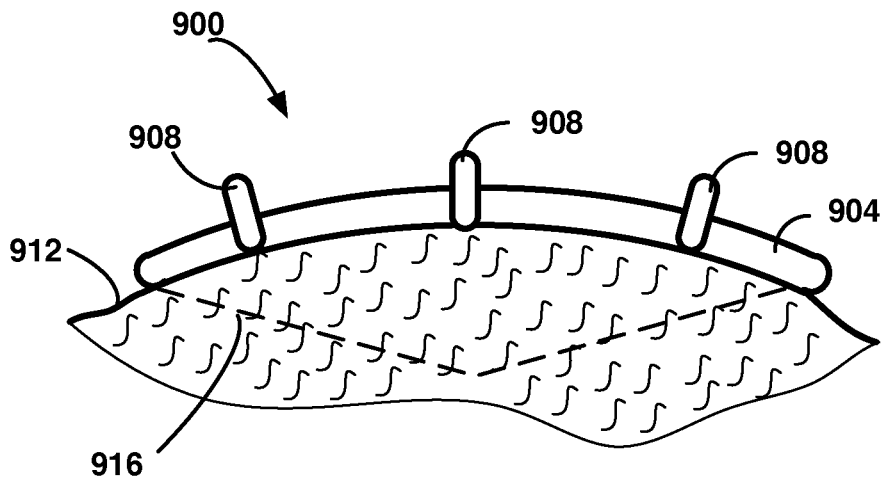
FIG. 9 is a schematic illustration of a forth exemplary embodiment of the present applicator configured to apply ultrasound energy to a segment of skin.

FIG. 9 is a schematic illustration of a forth exemplary embodiment of the present applicator configured to apply ultrasound energy to a segment of the skin formed as a protrusion. Ultrasound energy is another type of skin heating energy. The ultrasound energy is applied to the skin of a subject with the help of an applicator 900, which may include a conventional ultrasound transducer 904 and one or more temperature probes 908 arranged to provide the temperature of the treated skin section 912. Transducer 904 may be of a curved or flat shape and configured for convenient displacement over the skin. Lines 916 schematically show skin volume 912 heated by the ultrasound energy/waves.

Figure 10:
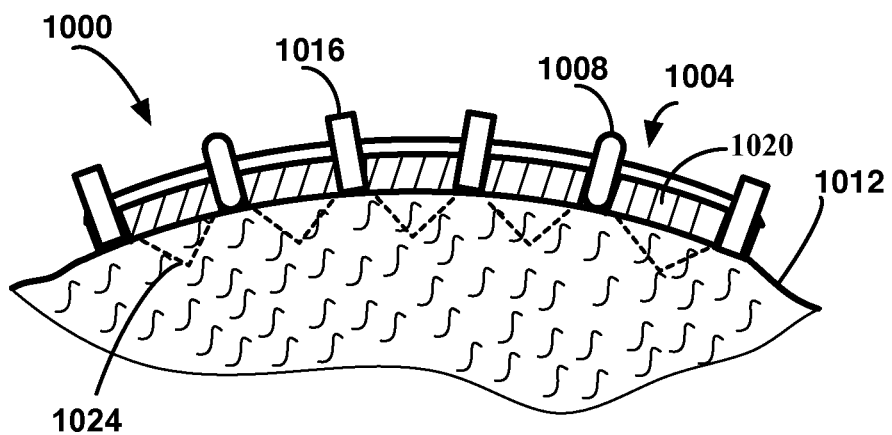
FIG. 10 is a schematic illustration of a fifth exemplary embodiment of the present applicator configured to apply ultrasound energy and optical radiation to a segment of skin.

FIG. 10 is a schematic illustration of a fifth exemplary embodiment of the present applicator configured to apply ultrasound energy and optical radiation to a segment of the skin. The ultrasound energy is applied to skin 1012 of a subject with the help of an applicator 1000, which may include a phased array ultrasound transducer 1004, one or more temperature probes 1008 arranged to provide the temperature of the treated skin segment 1012, and one or more optical radiation sources 1016. Individual elements 1020 forming transducer 1004 may be arranged in a desired order and emit ultrasound energy 1024 to heat the desired depth of skin segment 1012. Optical radiation sources 1016 may be configured to irradiate the same skin segment 1012 treated by ultrasound, accelerating generation of the desired skin effect.

Figure 11:
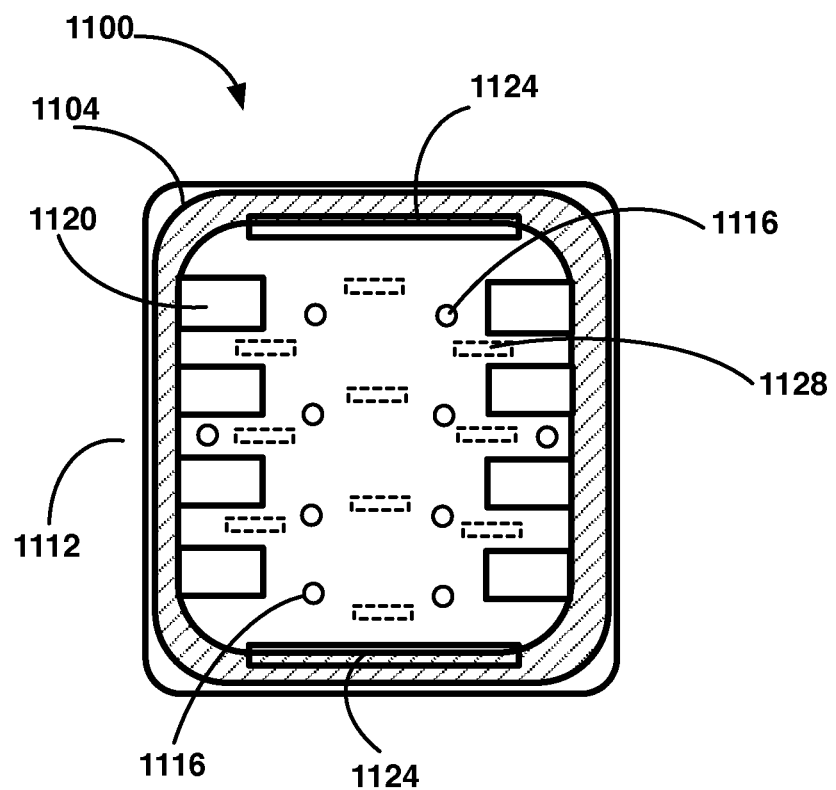
FIG. 11 is a schematic illustration of a sixth exemplary embodiment of the present applicator configured to apply RF energy, ultrasound energy, and optical radiation to a segment of skin.

FIG. 11 is a schematic illustration of a sixth exemplary embodiment of the present applicator configured to apply RF energy, ultrasound energy, and optical radiation to a segment of the skin. FIG. 11 is a top view of an applicator 1100 configured for application to a segment of skin 1112. Applicator 1100 includes a bell shaped case 1104 and may include one or more ultrasound wave transducers 1120 configured to couple ultrasound energy to skin 1112, one or more RF energy supplying electrodes 1124, and one or more sources of optical radiation 1128. Applicator 1100 further includes one or more temperature probes 1116 similar to the earlier described temperature probes. Ultrasound wave transducers 1120 are configured to cover as large as possible segment of skin 1112. RF energy supplying electrodes 1124 may be arranged to provide a skin heating current in the direction perpendicular to that of propagation of ultrasound energy. Presence of firm contact of skin 1112 with electrodes 1124 may be detected, for example by measuring the skin impedance. Firm contact of skin 1112 with ultrasound wave transducers 1120 may be detected by measuring the power of reflected ultrasound energy from the skin 1112.

Figure 12:
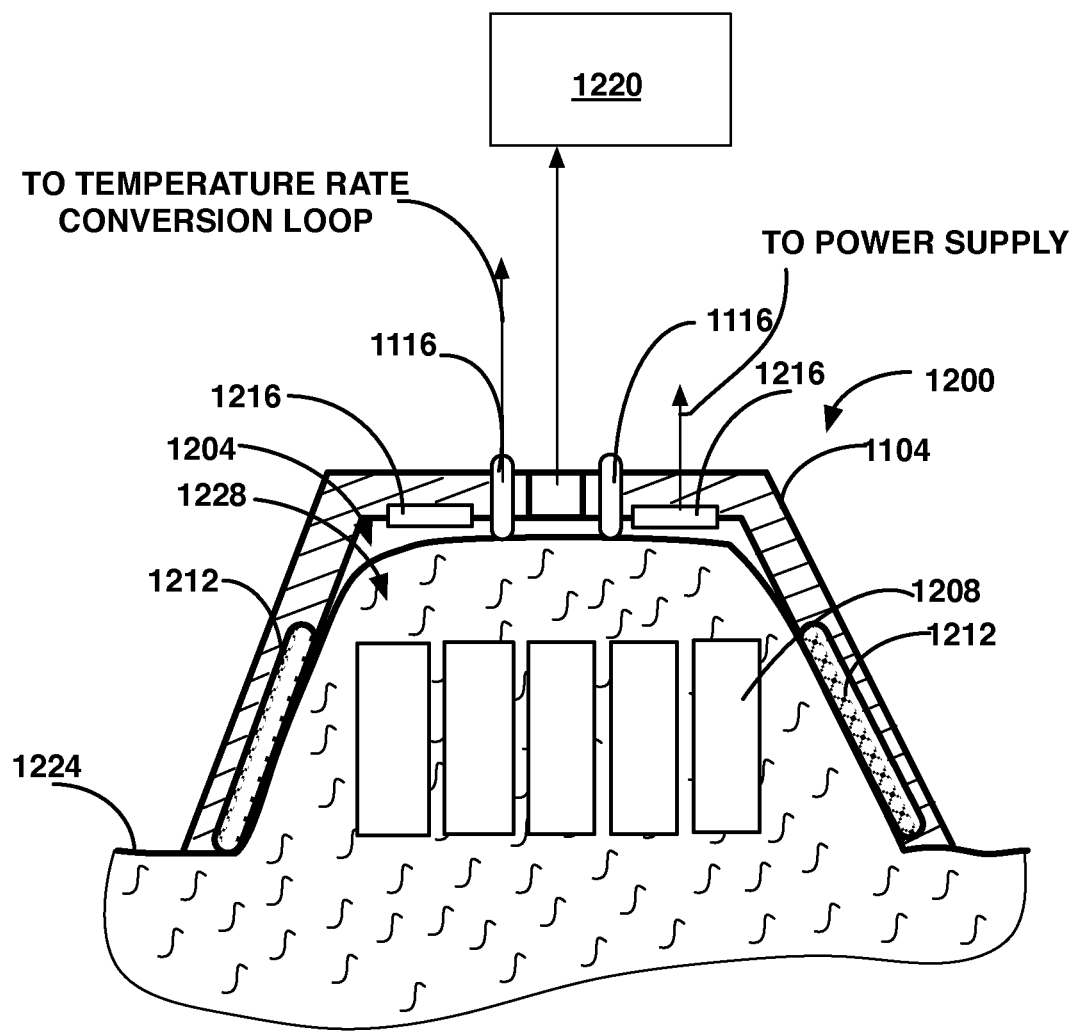
FIG. 12 is a schematic illustration of a seventh exemplary embodiment of the present applicator configured to apply RF energy, ultrasound energy, and optical radiation to a segment of skin formed as a protrusion.

FIG. 12 is a schematic illustration of an eighth exemplary embodiment of the present applicator configured to apply RF energy, ultrasound energy, and optical radiation to a segment of the skin formed as a protrusion. Applicator 1200 is a bell shaped case 1104 with inner segment 1204 containing one or more ultrasound wave transducers 1208, one or more RF energy supplying electrodes 1212 and optionally one or more sources of optical radiation 1216. A vacuum pump 1220 is connected to the inner segment 1204 of applicator 1200. When applicator 1200 is applied to skin 1224, the inner segment 1204 becomes hermetically closed or at least sufficiently sealed to enable the creation of a temporary vacuum. Operation of vacuum pump 1220 evacuates air from inner segment 1204. Negative pressure in inner segment 1204 draws skin 1224 into inner segment 1204 forming a skin protrusion 1228. As skin protrusion 1228 grows, it occupies a larger volume of inner segment 1204, and spreads in a uniform way inside the segment. The protrusion spreading enables firm contact of skin 1224 with electrodes 1212. When firm contact between skin protrusion 1228 and electrodes 1212 is established, RF energy is supplied to skin protrusion 1228. Presence of firm contact of skin 1224 with electrodes 1212 may be detected for example, by measuring the skin protrusion 1224 impedance, as explained hereinabove.

Applicator 1200 further includes one or more ultrasound wave transducers 1208 configured to couple ultrasound energy to skin protrusion 1228. Ultrasound transducers 1208 may be conventional transducers or phased array transducers.

Applicator 1200 and other applicators described may contain additional devices supporting skin and electrodes cooling, auxiliary control circuits, wiring, and tubing not shown for the simplicity of explanation. A thermo-electric cooler or a cooling fluid may provide cooling. The cooling fluid pump, which may be placed in a common control unit housing.

For skin treatment procedures, the user couples the applicator to a segment of skin, activates one or more sources of skin heating energy and applies the energy to the skin. For example, applying RF energy or ultrasound energy to skin, or irradiating the skin with optical radiation. RF energy interacts with the skin inducing a current in the skin that heats at least the segment located between the electrodes. The heat produces the desired effect on the skin, which may be wrinkle removal, hair removal, collagen shrinking or destruction, and other cosmetic and skin treatments. In order to improve RF to skin coupling the treated skin segment may be first coated by a layer of suitable gel typically having resistance higher than that of the skin.

Ultrasound energy causes skin cells mechanical vibrations. Friction between the vibrating cells heats the skin volume located between the transducers and enables the desired treatment effect, which may be body shaping, skin tightening and rejuvenation, collagen treatment, removal of wrinkles and other aesthetic skin treatment effects.

Application of optical radiation of proper wavelength to skin causes an increase in skin temperature because the skin absorbs at least some of the radiation. Each of the mentioned skin heating energies may be applied to the skin alone or in any combinations of them to cause the desired skin effect.

For skin treatment, the user or operator continuously displaces the applicator across the skin. When the user displaces the applicator at a speed slower than the desired or proper speed, an indicator, such as an audio signal, can be activated to attract the user's attention and thereby to help avoid or alleviate the risk of potential skin burns. The temperature sensor continuously measures temperature and may shut down RF energy supply when the rate of temperature increase or change is too fast or when the absolute temperature measured exceeds the preset limit. When the user displaces the applicator at a speed higher than the desired or proper speed, the rate of temperature change is slower than desired. An indicator, such as a visual signal indicator can be activated to attract the user's attention and thereby to help avoid or alleviate the formation of poorly treated or under-treated skin segments. This maintains the proper efficacy of skin treatment. It should be appreciated that the indicators as presented are just a non-limiting example and any of a variety of types of indicators including speakers, buzzers, vibrators, lights, etc can be used for any of the various alerting requirements.

The applicator may be configured to automatically change the RF energy coupled to the skin. In such mode of operation, where the applicator is displaced at an almost constant speed, a controller based on the rate of temperature change may automatically adjust the value or magnitude of RF energy coupled to the skin. For example, at a high rate of temperature change the magnitude of RF energy coupled to the skin will be adapted and reduced to match the applicator displacement speed. At lower rates of temperature change, the magnitude of RF energy coupled to the skin will be increased to match the applicator displacement speed. The user or operator may be concurrently alerted in a manner disclosed hereinabove. This mode of operation also maintains the proper efficacy of skin treatment.

A number of embodiments have been described. Nevertheless, it will be understood that various modifications may be made without departing from the spirit and scope of the method. Accordingly, other embodiments are within the scope of the following claims:

What is claimed is:
1. An applicator for applying one or more types of skin heating energy to a subject skin, said applicator comprising:
one or more sources of skin heating energy configured to apply said energy to the subject skin;
a temperature sensor operative to provide a continuous indication of the subject skin temperature during displacement of the applicator across the skin;
a mechanism configured to convert said temperature into a rate of temperature change; and
a mechanism configured to continuously monitor and indicate the quality of the coupling of at least one type of skin heating energy to the subject skin; and
a mechanism configured, during course of operation, to eliminate the influence of the electrode-skin contact on the rate of temperature variations and derive from the temperature indication and quality of coupling of skin heating energy to the subject skin, a rate of temperature change.

2. The applicator according to claim 1, wherein at least one of the source of skin heating energies is selected from a group of skin heating energy sources consisting of optical radiation source configured to irradiate the subject skin, RF energy source configured to apply to the subject skin RF energy with one or more RF electrodes, and a source of ultrasound energy configured to employ one or more ultrasound transducers to apply ultrasound energy to the subject skin.

3. The applicator according to claim 2, wherein said RF electrodes are selected from a group of RF electrodes consisting of electrodes having elongated and curved bodies.

4. The applicator according to claim 2, wherein said RF electrodes are made of one of a group of materials consisting of heat conductive metal, metal coated plastic or composite material.

5. The electrodes according to claim 2, wherein said RF electrodes are selected from a group of electrodes consisting of solid, flexible, and hollow electrodes.

6. The electrodes according to claim 2, wherein said RF electrodes are detachable electrodes.

7. The applicator according to claim 2, wherein said ultrasound transducers are selected from a group of ultrasound transducers consisting of conventional and phased array transducers.

8. The applicator according to claim 1, wherein the temperature sensor is selected from a group of temperature sensors consisting of thermistor, thermocouple, resistance temperature detectors, and a pyrometer.

9. The applicator according to claim 8, wherein the temperature sensor is associated with at least one temperature probe.

10. The applicator according to claim 8, wherein the temperature sensor is associated with at least one RF electrode.

11. The applicator according to claim 2, wherein the source of optical radiation is selected from a group of sources consisting of incandescent lamps and lamps optimized for emission of red and infrared radiation and a reflector, Intense Pulse Light source, a LED, and a laser diode.

12. The applicator according to claim 1, further comprising gel dispenser.

13. The applicator according to claim 1, further comprising a visual signal indicator and an audio signal indicator, said indicators being configured to provide the status of interaction of the skin heating energy with the skin.

14. The applicator according to claim 13, wherein the visual signal indicator is configured to indicate that applicator displacement speed is faster than proper displacement speed and the audio indicator is operative to signify that the applicator displacement speed is slower than the proper applicator displacement speed.

15. The applicator according to claim 13, wherein the visual signal indicator is operative to indicate that the skin heating energy level is too lower, and the audio indicator is operative to signify that the skin heating energy level is too high.

16. The applicator according to claim 1, wherein the one or more types of skin heating energy is one of a group consisting of an optical radiation source, RF energy source, and ultrasound energy source; and
wherein:
- the optical radiation source couples the optical radiation to the skin by irradiating the segment of the skin between the RF electrodes;
- the RF energy source applies RF energy to the skin by contact of one or more RF electrodes with the skin; and
- the ultrasound energy source applies ultrasound energy to the skin by coupling one or more ultrasound energy transducer with the skin.

* * * * *